United States Patent [19]

Hollub

[11] Patent Number: 5,588,439
[45] Date of Patent: Dec. 31, 1996

[54] ACOUSTIC IMPULSE RESPIROMETER AND METHOD

[75] Inventor: Seth D. Hollub, Overland Park, Kans.

[73] Assignee: Nellcor Incorporated, Pleasanton, Calif.

[21] Appl. No.: 370,623

[22] Filed: Jan. 10, 1995

[51] Int. Cl.⁶ ........................................................ A61B 5/08
[52] U.S. Cl. ........................ 128/721; 128/660.02; 128/782
[58] Field of Search ........................................ 128/721, 716, 128/660.02, 661.02, 671, 782; 340/573, 575

[56] References Cited

U.S. PATENT DOCUMENTS

| | | | |
|---|---|---|---|
| 3,911,899 | 10/1975 | Hattes | 128/721 |
| 4,122,427 | 10/1978 | Karsh | 340/1 R |
| 4,197,856 | 4/1980 | Northrop | 128/660 |
| 4,306,567 | 12/1981 | Krasner | 128/671 |
| 4,635,198 | 1/1987 | Hohlweck et al. | 128/660.02 |
| 4,967,751 | 11/1990 | Sterzer | 128/653 |
| 5,220,922 | 6/1993 | Barany | 128/660 |
| 5,360,008 | 11/1994 | Campbell, Jr. | 128/671 |

*Primary Examiner*—Lee S. Cohen
*Attorney, Agent, or Firm*—Nawrocki, Rooney & Sivertson

[57] ABSTRACT

An apparatus and method for sensing respiratory motion to detect sleep apnea and the like. An acoustic pulse stimulator or generator located on one side of a body sends impulses through the body to impinge on one or more sensors on the opposite side of the body. Because time delay between transmitter and receiver is determined by distance, and because distance is directly related to breathing motions of the body, measurement of the time delay will have a direct correspondence to breathing motions.

15 Claims, 3 Drawing Sheets

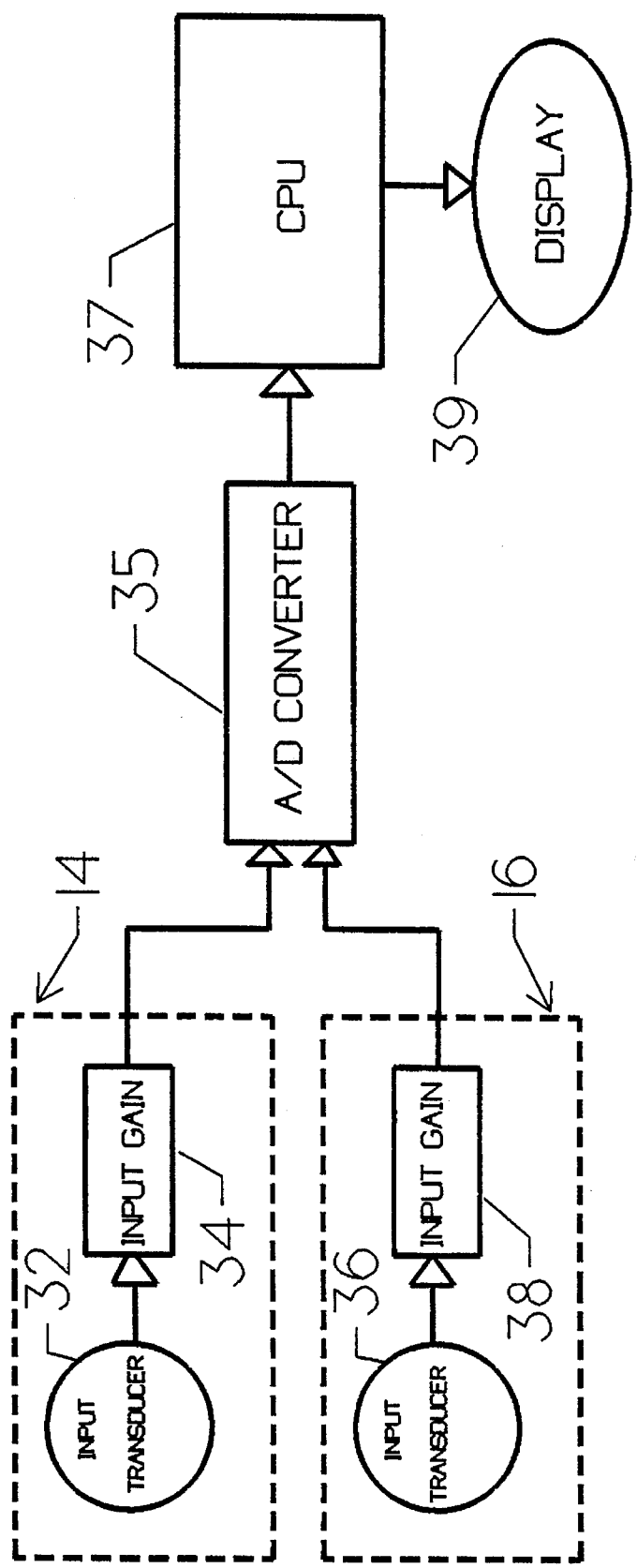

ACOUSTIC IMPULSE RESPIROMETER AND METHOD

CROSS REFERENCE TO CO-PENDING APPLICATIONS +ps None.

BACKGROUND OF THE INVENTION

1. Field of the Invention

The present invention generally relates to medical monitors: more specifically to electrical sensing apparatus for sensing body functions and still more specifically to an apnea respirometer utilizing acoustic impulses that are transmitted through the body.

2. Description of the Prior Art

Apnea measurement apparatus have been known in the art for some time, including electrical respirometers.

It is known that apnea is often measured with impedance respirometry. In general, a low current, medium frequency (20 KHz to 100 KHz) signal is passed through the thorax to sensors from which the impedance is calculated. The current path is selected such that variations in impedance will correspond to breathing motion.

This form of apnea measurement has certain disadvantages including potential interference with passive ECG measurements; probable reliance on ECG sensors; sensitivity to cardiac generated electrical signals and cardiac artifacts; and, sensitivity to ambient electrical noise and to direct electrical contact and current flow through the patient.

It is also known that apnea may be measured with airflow temperature sensing techniques, which techniques have the disadvantages, for example, of the airflow sensor blocking the nose or mouth, and sensitivity to ambient temperature and airflow conditions.

U.S. Pat. No. 5,220,922 teaches an ultrasonic medical motion monitoring device which bounces transduced sound waves off moving objects in the body, such as the heart, and reads the phase changes in the echo-return waves. This is similar to the prior art use of ultrasonic waves and carries the same disadvantages discussed above.

U.S. Pat. Nos. 4,197,856 and 4,122,427 also disclose ultrasonic body motion detectors.

U.S. Pat. No. 4,306,567 discloses a pressure sensor used to monitor body rhythmic functions by detecting pressure waves within a narrow bandwidth, the frequency being centered about 400 Hz for monitoring lung motion, and 45 Hz for monitoring cardiac activity.

U.S. Pat. No. 4,967,751 detects breathing rate with Doppler frequency shift by monitoring the cyclical movement of the thorax.

SUMMARY OF THE INVENTION

The present invention overcomes the disadvantages found in the prior art by providing an apnea respirator having at least one acoustic stimulator or transmitter and at least one acoustic receiver or sensor on essentially opposite sides of the torso of a patient, such that transmitted stimulation pulses propagate through the desired portion of the body to the receiver. Acoustic impulses transmitted through a moving portion of the body, for example the chest, will have a delay factor corresponding to distance. Thus, as the chest moves, the pulses sensed at the receiver will have travelled varying distances related to chest breathing motion.

It is well known to those of skill in the art that the primary problems that exist in the design of respiration detection apparatus are ambient noise and patient-generated signals. The apparatus of this invention solves or greatly reduces the effects of these problems in a manner more fully described below.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the following figures:

FIG. 3 is a block diagram of a pair of acoustic waveform receivers as may be used in the preferred embodiment of this invention shown connected to circuitry for calculating and displaying the value of received signals.

DETAILED DESCRIPTION OF THE PREFERRED EMBODIMENTS

Figure 1:
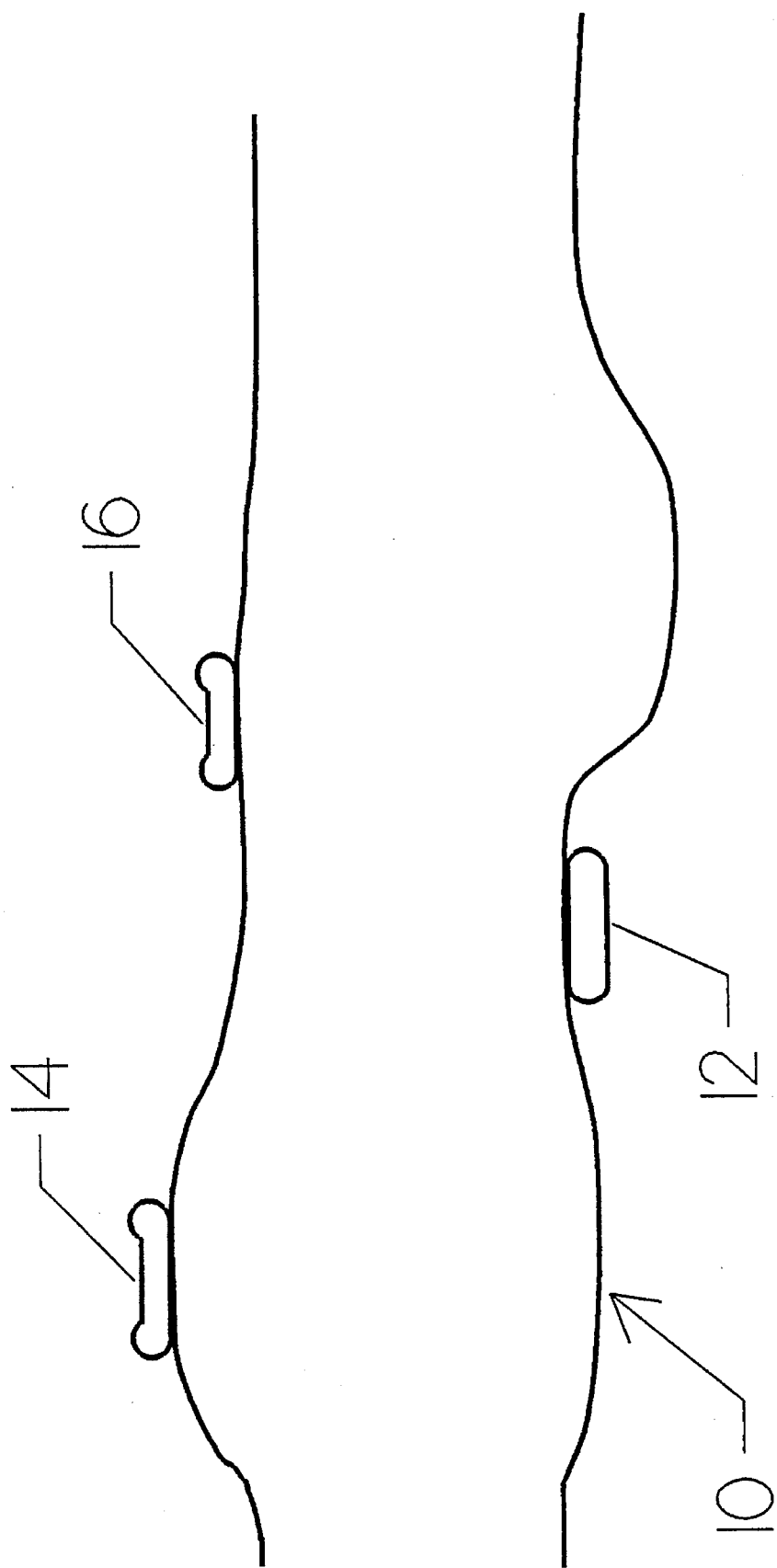
FIG. 1 is a diagram representative of a human torso showing how the apparatus of this invention may be placed on a body.

FIG. 1 depicts a representation of a human torso 10. An acoustic stimulator or transmitter 12, preferably a piezoelectric transducer, is preferably placed on the back of torso 10. A first acoustic sensor or receiver 14 is preferably placed on the chest of torso 10, and a second acoustic sensor or receiver 16 is preferably placed on the stomach of torso 10. In this preferred embodiment of FIG. 1, it is desirable to assure that receivers 14 and 16 are placed on torso such that they lie on opposite sides of the body's diaphragm.

It will be recognized that the number of acoustic receivers can be varied without departing from the spirit of this invention as depicted in FIG. 1. When a single receiver is used it is desirable to place it on torso 10 at a point below the body's sternum.

A selected series of sound waves is supplied to torso 10 by transmitter 12. These waves propagate through torso 10 to impinge on and be sensed by acoustic receivers 14 and 16. Because the time delay between impulse generation and impulse reception corresponds directly to distance, and because distance within torso 10 corresponds directly to breathing motion, then the time delay relates directly to the breathing motion. In the preferred embodiment of FIG. 1, two independent distances can be calculated; the chest distance of torso 10 and the stomach distance of torso 10; and thus the apparatus of this invention accounts for two types of respiration.

As is more fully described below, by selecting a stimulator 12 that provides a large number of impulses over a short period of time, ambient noise can be rejected. Further, by selecting a proper pulse bandwidth, patient-generated noises can be eliminated from detection by receivers 14 and 16.

Figure 2:
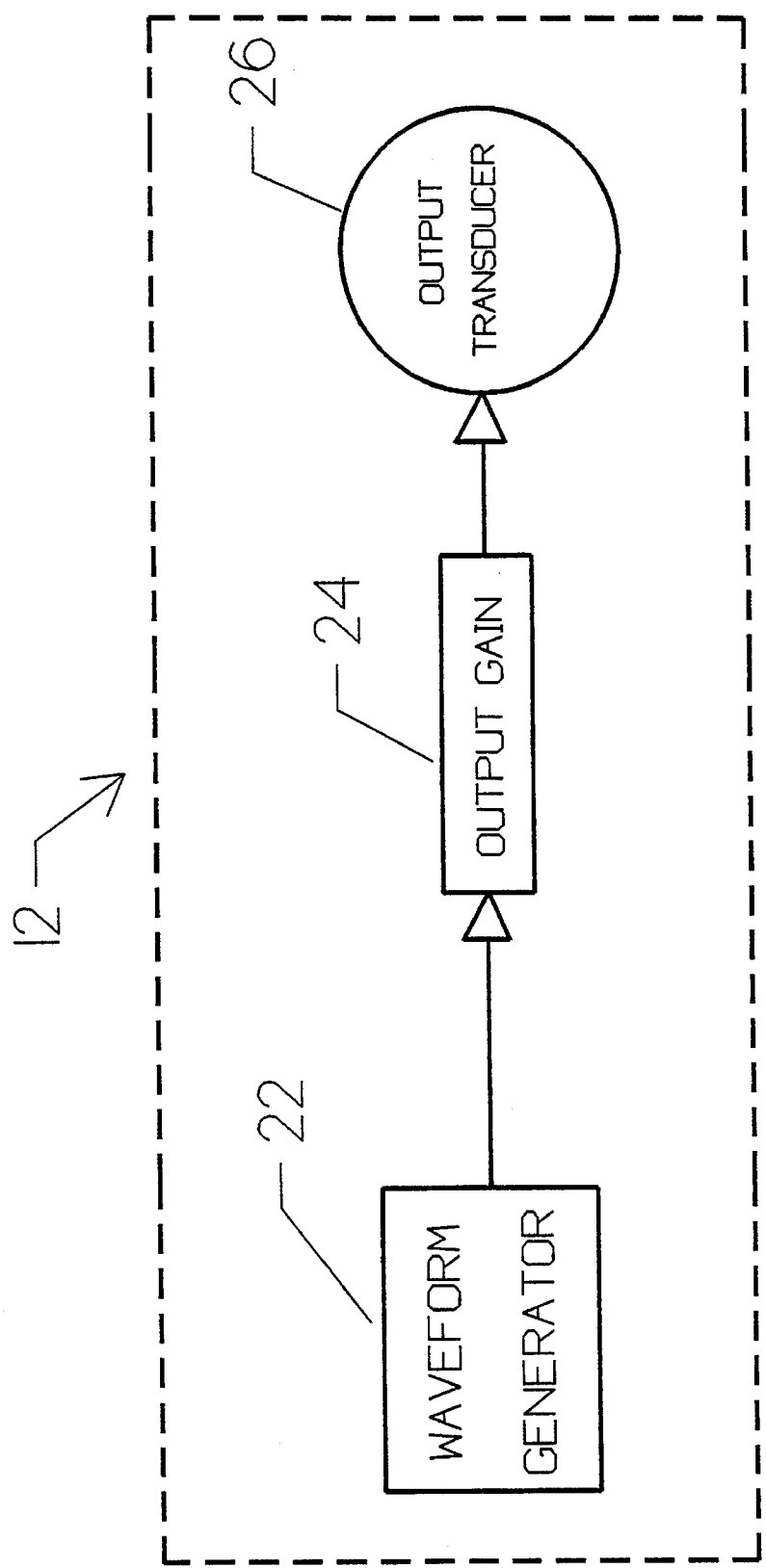
FIG. 2 is a block diagram of an acoustic waveform transmitter as may be used in the preferred embodiment of this invention.

FIG. 2 depicts stimulator or transmitter 12 in block diagram. Transmitter 12, in a dashed lined rectangle, comprises a waveform generator 22, an output gain amplifier 24, and an output transducer 26. The selected stimulating impulses are formulated in generator 22, amplified by gain amplifier 24 and applied to output transducer 26 for transmition through a body. Preferably, the impulses from generator 22 lie in the range of 200 KHz to 500 KHz. Though this bandwidth is within the ultrasonic, it is well below typical frequencies used in the prior art for medical ultrasound imaging, and is well above the sensible sonic range.

Referring now to FIG. 3, there is shown the pair of acoustic receivers of FIGS. 1, 14 and 16. Sensor or receiver 14 comprises an input transducer 32 and an input gain amplifier 34. Sensor or receiver 16 comprises an input transducer 36 and an input gain amplifier 38. Also shown in FIG. 3 is circuitry for calculation and display of the signal received by sensor 14 and 16, which circuitry comprises an analogue-to-digital converter 35, a computer or CPU 37 and a display unit 39.

Acoustic impulses from stimulator 12 propagate through torso 10 and are then sensed by input transducers 32 and 36, and the sensed signals from transducers 32 and 36 are then amplified by, respectively, amplifiers 34 and 38. The amplified signals from input gain amplifiers 34 are sent to A/D converter 35 which in turn sends digital signals to CPU 37 for calculation of the breathing motion and display on unit 39.

Proper placement of sensors 14 and 16 on torso 10 as in the preferred embodiment of FIG. 1 will result in independent calculations of two types of breathing motions, namely chest and stomach breathing, which can be displayed separately on unit 39. If desired, a single sensor can be used to sense the sonic impulses from stimulator 12, or if desired, a plurality of sensors greater than two can be employed to receive the propagate acoustic signals.

The actual method of detection of the propagated signals can vary according to the type and sensitivity of the stimulator and receiver. The simplest method would be to detect the rising amplitude of the first arriving transmitted impulse and measure the time interval between sending and receiving. This simple form of detection will only be reliable when the sensors or receivers are constructed to have a lower Q and higher resonance frequency.

An alternate way to detect the variable delay of the propagated impulses is to search for the higher amplitude cycles in the sensed or received envelope of impulses and then detect zero-crossings. By repeating the transmitted pulse train frequently, variations in the time of the selected zero-crossings can be tracked more accurately than rise-time detection.

As stated above, patient-generated signals and ambient noise are the major problems which face any respiration technique. Any such system must be able to function reliably through talking, wheezing, coughing, moving and normal ambient electrical and acoustic noise in the home or hospital. Further, cardiac events must not confuse the system, even when breath rate and cardiac rate are identical.

The apparatus of the present invention overcomes the problems of patient-generated signals and ambient noise primarily through the careful choice of the band of interest and the selectivity of the sensors as regards that bandwidth. It is apparent that signals outside the chosen bandwidth will be rejected by the sensor selectivity and filtering, thus confining the received or sensed energy to the band of interest. By using a sensor with a poor response to signals inside the sensible acoustic range (20 Hz–20 KHz), ambient acoustic noises are rejected thus eliminating interference from talking, coughing and heart beat sounds, for example. It is empirically known that essentially no noise above 20 KHz is generated by a human being.

Additional noise rejection is achieved through use of the present invention by repeating the noise train with sufficient frequency to average adjacent pulse reception buffers together. Except when the pulses are exactly synchronous with a repetitive ambient noise event, such noises are reduced in amplitude by approximately the square root of the number of repetitions averaged. The present invention can allow for approximately 100 averages per sample, with a corresponding factor of 10 reduction in noise response.

Having thus described the preferred embodiments of the present invention, those of skill in the art will readily appreciate the other useful embodiments within the scope of the claims hereto attached.

I claim:

1. A detector for measuring motion of a patient's body during respiration, comprising:

an acoustic impulse generator adapted to be disposed at a first position on the patient's body;

an acoustic impulse receiver adapted to be disposed at a second position on the patient's body, being disposed in spaced relationship to the acoustic impulse generator to detect impulses therefrom upon passage of the impulses through the patient's body; and means for determining changes in a spaced relationship distance between the acoustic impulse generator and the acoustic impulse receiver induced by the patient's respiration.

2. The detector of claim 1 including a plurality of said acoustic impulse receivers for mounting in spaced relation on the patient's body.

3. The detector of claim 1 including display means connected to said means for determining for visually displaying data based on calculations by said means for determining changes in spaced relationship distance.

4. The detector of claim 1 in which said generator provides acoustic impulses at a frequency above the sensible sound frequency of a human.

5. The detector of claim 4 in which the acoustic impulses are provided in the frequency range of 200 KHz to 500 KHz.

6. The method of measuring motion of the body of a patient comprising the steps of:

a. propagating acoustic impulses through at least one movable portion of the body from a first position on the body;

b. detecting the propagated impulses at least a second position on the body substantially opposite the first position; and c. measuring motion of the body portion based on the detected impulses.

7. The method of claim 6 including the step of:

propagating the acoustic impulses at a frequency above the sensible sound frequency of a human.

8. The method of claim 6 including the step of:

propagating the acoustic impulses within the frequency range of 200 KHz to 500 KHz.

9. The method of claim 6 including the step of:

detecting propagated acoustic impulses within the bandwidth of 200 KHz to 500 KHz.

10. The method of claim 9 including the step of:

calculating the distance traveled by the detected acoustic impulses between propagation and detection.

11. The method of claim 10 including the step of:

calculating the respiration rate of the patient from the distance traveled by the detected acoustic impulses.

12. The method of claim 11 including the step of:

displaying the calculated rate.

13. The method of claim 6 including the step of:

calculating the distance traveled by the detected acoustic impulses between propagation and detection.

14. The method of claim 13 including the step of:

calculating the respiration rate of the patient from the distance traveled by the detected acoustic impulses.

15. The method of claim 14 including the step of:

displaying the calculated rate.

* * * * *